United States Patent
Langley, II et al.

(10) Patent No.: US 11,896,357 B2
(45) Date of Patent: *Feb. 13, 2024

(54) SYSTEMS AND METHODS FOR DETECTING PHYSICAL CHANGES WITHOUT PHYSICAL CONTACT

(71) Applicant: Life Detection Technologies, Inc., Sunnyvale, CA (US)

(72) Inventors: John B. Langley, II, Half Moon Bay, CA (US); Guy McIlroy, Los Gatos, CA (US)

(73) Assignee: Life Detection Technologies, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/052,655

(22) Filed: Nov. 4, 2022

(65) Prior Publication Data

US 2023/0115139 A1    Apr. 13, 2023

Related U.S. Application Data

(63) Continuation of application No. 17/316,131, filed on May 10, 2021, now Pat. No. 11,523,745, which is a
(Continued)

(51) Int. Cl.
*G01R 29/12*  (2006.01)
*A61B 5/05*  (2021.01)
(Continued)

(52) U.S. Cl.
CPC .............. *A61B 5/05* (2013.01); *A61B 5/725* (2013.01); *A61B 5/7228* (2013.01);
(Continued)

(58) Field of Classification Search
CPC .... G01R 29/08; G01R 29/0814; G01N 27/22; G08B 21/02; G08B 21/0211
See application file for complete search history.

(56) References Cited

U.S. PATENT DOCUMENTS

| 4,182,315 A | 1/1980 | Vas et al. |
| 4,532,501 A | 7/1985 | Hoffman |
| (Continued) | | |

FOREIGN PATENT DOCUMENTS

| CN | 1424577 A | 6/2003 |
| CN | 1630822 A | 6/2005 |
| (Continued) | | |

OTHER PUBLICATIONS

International Search Report and Written Opinion, dated Dec. 13, 2019, for International Application No. PCT/US2019/052076 (10 pages).

(Continued)

*Primary Examiner* — Thang X Le
(74) *Attorney, Agent, or Firm* — Weaver IP L.L.C.

(57) ABSTRACT

Systems and methods are provided for detecting and analyzing changes in a body. For example, a system includes an electric field generator configured to produce an electric field. The system includes an external sensor device configured to detect physical changes in the electric field, where the physical changes affect amplitude and frequency of the electric field. The system includes a quadrature demodulator configured to detect changes of the frequency of the output of the electric field generator. The system includes an amplitude reference source and an amplitude comparison switch configured to detect changes of the amplitude of the output of the electric field generator. The system includes a signal processor configured to analyze the changes of the amplitude and frequency of the output of the electric field generator.

20 Claims, 7 Drawing Sheets

Related U.S. Application Data continuation of application No. 16/058,821, filed on Aug. 8, 2018, now Pat. No. 11,026,593, which is a continuation of application No. 15/418,328, filed on Jan. 27, 2017, now Pat. No. 10,080,507.

(60) Provisional application No. 62/287,598, filed on Jan. 27, 2016.

(51) Int. Cl.
    *A61B 5/00*     (2006.01)
    *G01R 29/08*     (2006.01)
    *A61B 5/08*     (2006.01)
    *A61B 5/024*     (2006.01)

(52) U.S. Cl.
CPC ............ *A61B 5/7278* (2013.01); *A61B 5/742* (2013.01); *G01R 29/0814* (2013.01); *A61B 5/024* (2013.01); *A61B 5/0816* (2013.01); *A61B 5/7225* (2013.01)

(56) References Cited

U.S. PATENT DOCUMENTS

| | | | |
|---|---|---|---|
| 4,788,869 A | 12/1988 | Li | |
| 4,958,638 A | 9/1990 | Sharpe et al. | |
| 5,434,887 A | 7/1995 | Osaka | |
| 6,020,784 A | 2/2000 | Fujii | |
| 6,339,623 B1 | 1/2002 | Iwamatsu | |
| 6,356,746 B1 | 3/2002 | Katayama | |
| 6,679,830 B2 | 1/2004 | Kolarovic et al. | |
| 7,109,726 B2 | 9/2006 | van Berkel | |
| 7,173,525 B2 | 2/2007 | Albert | |
| 7,242,728 B2 | 7/2007 | Kanazawa | |
| 7,383,071 B1 | 6/2008 | Russell et al. | |
| 7,445,605 B2 | 11/2008 | Overall et al. | |
| 7,885,700 B2 | 2/2011 | Clark et al. | |
| 7,887,708 B2 | 2/2011 | Chew | |
| 7,952,425 B2 | 5/2011 | Zhang et al. | |
| 8,057,388 B1 | 11/2011 | Russell et al. | |
| 8,274,386 B2 | 9/2012 | Dea et al. | |
| 8,842,010 B2 | 9/2014 | Cehelnik | |
| 8,994,536 B2 | 3/2015 | Margon | |
| 9,035,778 B2 | 5/2015 | Howie et al. | |
| 9,060,745 B2 | 6/2015 | Su et al. | |
| 9,204,802 B2 | 12/2015 | Feldman et al. | |
| 9,285,889 B2 | 3/2016 | Bateman et al. | |
| 9,549,682 B2 | 1/2017 | Howie et al. | |
| 9,685,996 B1 | 6/2017 | Thoen | |
| 9,921,706 B2 | 3/2018 | Kim et al. | |
| 10,080,507 B2 | 9/2018 | Langley, II et al. | |
| 11,026,593 B2 | 6/2021 | Langley et al. | |
| 2002/0013538 A1 | 1/2002 | Teller | |
| 2002/0032016 A1 | 3/2002 | Ji | |
| 2003/0021078 A1 | 1/2003 | van Berkel | |
| 2004/0100376 A1 | 5/2004 | Lye et al. | |
| 2004/0181703 A1 | 9/2004 | Lilja et al. | |
| 2004/0201384 A1* | 10/2004 | Berkel ..................... G01D 5/24 324/604 |
| 2004/0250192 A1 | 12/2004 | Kanazawa | |
| 2004/0260346 A1 | 12/2004 | Overall et al. | |
| 2005/0104670 A1 | 5/2005 | Naviasky et al. | |
| 2005/0273218 A1 | 12/2005 | Breed et al. | |
| 2006/0154642 A1 | 7/2006 | Scannell | |
| 2006/0158173 A1 | 7/2006 | Takiguchi | |
| 2006/0261818 A1 | 11/2006 | Zank et al. | |
| 2007/0139049 A1* | 6/2007 | Van Berkel ......... G06V 40/1306 324/452 |
| 2007/0285296 A1 | 12/2007 | Bilhan | |
| 2008/0007445 A1 | 1/2008 | Leach et al. | |
| 2008/0074307 A1 | 3/2008 | Boric-Lubecke et al. | |
| 2008/0259043 A1 | 10/2008 | Buil et al. | |
| 2009/0048500 A1 | 2/2009 | Corn | |
| 2009/0240160 A1 | 9/2009 | Thompson et al. | |
| 2009/0318779 A1 | 12/2009 | Tran | |
| 2010/0152600 A1 | 6/2010 | Droitcour et al. | |
| 2010/0201355 A1 | 8/2010 | Yamaguchi et al. | |
| 2010/0231234 A1 | 9/2010 | Tateishi et al. | |
| 2013/0267791 A1 | 10/2013 | Halperin et al. | |
| 2013/0285672 A1 | 10/2013 | Russell et al. | |
| 2014/0055269 A1 | 2/2014 | Howie et al. | |
| 2014/0140444 A1 | 5/2014 | Onishi et al. | |
| 2014/0222110 A1 | 8/2014 | Kibler et al. | |
| 2015/0031964 A1 | 1/2015 | Bly et al. | |
| 2015/0057557 A1 | 2/2015 | Howie et al. | |
| 2015/0212027 A1 | 7/2015 | Dhurjaty | |
| 2015/0276976 A1* | 10/2015 | Holenarsipur .......... G06F 1/169 250/338.1 |
| 2015/0317002 A1 | 11/2015 | King-Smith et al. | |
| 2016/0029556 A1 | 2/2016 | Legrand et al. | |
| 2016/0148034 A1 | 5/2016 | Kremin et al. | |
| 2016/0187277 A1 | 6/2016 | Potyrailo et al. | |
| 2017/0209085 A1 | 7/2017 | Langley, II et al. | |
| 2018/0092557 A1* | 4/2018 | Bickford ................ A61B 5/375 |
| 2018/0210582 A1 | 7/2018 | Kim et al. | |
| 2019/0029556 A1 | 1/2019 | Langley, II et al. | |
| 2021/0228103 A1* | 7/2021 | Richter .............. G06K 7/10366 |

FOREIGN PATENT DOCUMENTS

| | | |
|---|---|---|
| CN | 101277645 A | 10/2008 |
| CN | 104644143 A | 5/2015 |
| CN | 108601531 A | 9/2018 |
| EP | 2093588 A1 | 8/2009 |
| EP | 2886051 A1 | 6/2015 |
| EP | 3407778 B1 | 1/2021 |
| FR | 2923150 | 5/2009 |
| GB | 2062239 A | 5/1981 |
| JP | S60-142274 A | 7/1985 |
| JP | H07-288551 A | 10/1995 |
| JP | 2010-504155 A | 2/2010 |
| JP | 2010-537767 A | 12/2010 |
| JP | 2011-519288 A | 7/2011 |
| JP | 2012-073251 A | 4/2012 |
| JP | 2012-239748 A | 12/2012 |
| JP | 2014-210137 A | 11/2014 |
| JP | 2015-91358 A | 5/2015 |
| JP | 2015-205045 A | 11/2015 |
| JP | 2019-509473 A | 4/2019 |
| WO | WO-03/048789 | 6/2003 |
| WO | WO-2015/174879 | 11/2015 |
| WO | 2017/132514 A1 | 8/2017 |
| WO | WO-2018/137977 | 8/2018 |

OTHER PUBLICATIONS

Beardsmore-Rust, "Remote applications of electric potential sensors in electrically unshielded environments," Thesis submitted for Doctor of Philosophy, University of Sussex, 185 pages (Apr. 2010).

Buckley, "Plessey EPIC sensor makes a heart monitor in a wristwatch," EE Times Europe, 2 pages (May 6, 2012), <http://www.eetimes.com/General/PrintView/4372353>.

Business Wire, "PREE Corporation's Heartfelt Infant Vitals and Video Monitoring System is Now in Pre-Sales," PREE Corporation Press Release, 1 page (Feb. 15, 2012), <http://www.businesswire.com/news/home/20120215006285/en/PREE-Corporations-Heartfelt-Infant-Vitals-Video-Monitoring>.

Connor, "EPIC: A New Epoch in Electric Potential Sensing," 4 pages (2011).

Connor, "EPIC: Introducing Plessey's multi award winning EPIC Sensor and its many applications," 5 pages (2012) <http://www.plesseysemiconductors.com/products/epic/technical/>.

Germán-Salló, "Applications of Wavelet Analysis in ECG Signal Processing," Thesis submitted for Doctor of Philosophy, Technical University of Cluj-Napoca, 11 pages (2005).

Germán-Salló, "Processing of ECG Signals Using Wavelet Analysis," Acta Electrotehnica, vol. 46, No. 3, pp. 135-140, 6 pages. (2005).

International Search Report and Written Opinion for International Patent Application No. PCT/US2017/015345, dated Apr. 17, 2017 (9 pages).

(56) References Cited

OTHER PUBLICATIONS

PREE Corporation, "Heartfelt™ Infant Vitals & Video Monitoring System," 4 pages (2012), <http://www.technophysics.com/technology/heartfelt_baby_monitor>.
Royal College of Nursing, "Standards for assessing, measuring and monitoring vital signs in infants, children and young people," 16 pages (2011).
Saritha et al., "ECG Signal Analysis Using Wavelet Transforms," Bulg. J. Phys., vol. 35, pp. 68-77 (2008).
SBIR/STTR, "Non-Contact Monitor for Infants at Risk: Award Information," 2 pages (2012), <http//www.sbir.gov/sbirsearch/detail/156740>.
Venkataramanan, "Biosensor can monitor your heartbeat from a distance," ® Reed Business Information Ltd., 6 pages (Nov. 16, 2011).
Yan et al., "Verification of a non-contact vital sign monitoring system using an infant simulator," Abstract only, full article published as: Conf. Proc. IEEE Eng. Med. Biol. Soc., 1 page (2009) <http://www.ncbi.nlm.nih.gov/pubmed>.
Yan et al., "Verification of a non-contact vital sign monitoring system using an infant simulator," Conf. Proc. IEEE Eng. Med. Biol. Soc., pp. 4836-4839 (2009).
Extended European Search Report dated Aug. 21, 2019 received in related European Patent Application No. 17744973.3 (8 pages).
Office Action dated Oct. 13, 2020 received in related Japanese Patent Application No. 2018-539839 (8 pages).
Office Action dated Nov. 3, 2020 received in related Chinese Application No. 201780008413.6 (11 pages).
International Search Report dated Dec. 13, 2019 received in related PCT Application No. PCT/US19/52076 (10 pages).
S. Gabriel, et al., "The dielectric properties of biological tissues: III. Parametric models for the dielectric spectrum of tissues," Phys. Med. Biol. 41 (1996) pp. 2271-2293.
S. Guha et al., "An 8 Ghz CMOS Near Field Bio-sensor Array for Imaging Spatial Permittivity Distribution of Biomaterials," IEEE MTT-S International Microwave Symposium (IMS2014), 2014, pp. 1-4.
Ron, Kapusta et al., "Sampling Circuits That Break the kT/C Thermal Noise Limit" IEEE Journal of Solid-State Circuits, vol. 49, No. 8, Aug. 2014, 5 pages.
Chris D. Nikolopoulos, et al., "Auto Reconfigurable Patch Antenna for Biomedical Single Channel Multi-Frequency Microwave Radiometry Applications," Progress In Electromagnetics Research C, vol. 49 (2014), pp. 19-29.
Daniel Teichmann et al., "A Bendable and Wearable Cardiorespiratory Monitoring Device Fusing Two Noncontact Sensor Principles," IEEE Journal of Biomedical and Health Informatics, vol. 19, No. 3, May 2015, pp. 784-793.
Daniel Teichmann et al., "Noncontact Monitoring of Cardiorespiratory Activity by Electromagnetic Coupling," IEEE Transactions on Biomedical Engineering, vol. 60, No. 8, Aug. 2013, pp. 2142-2152.
Mikael Ekström et al., "Critical review of non-invasive respiratory monitoring in medical care," Medical & Biological Engineering & Computing—Aug. 2003, pp. 377-383.
TDC7200: Time-to-digital converter for time-of-flight (ToF) application for LIDAR and ultrasonic, Retrieved from the Internet URL: https://www.ti.com/product/TDC7200, published Jan. 8, 2015.
Office Action received for Canada Patent Application No. 3012319, dated Feb. 14, 2023, 3 pages.
Office Action received for Japanese Patent Application No. 2022-011295, dated Mar. 7, 2023, 9 pages (6 pages of English Translation and 3 pages of Official Copy).
Office Action received for Canada Patent Application No. 3012319, dated Nov. 21, 2023, 4 pages.

\* cited by examiner

SYSTEMS AND METHODS FOR DETECTING PHYSICAL CHANGES WITHOUT PHYSICAL CONTACT

CROSS-REFERENCE TO RELATED APPLICATIONS

This application is a continuation of U.S. patent application Ser. No. 17/316,131, filed May 10, 2021, which is a further continuation of U.S. patent application Ser. No. 16/058,821, filed Aug. 8, 2018, now U.S. Pat. No. 11,026,593, granted Jun. 8, 2021, which is further a continuation of U.S. patent application Ser. No. 15/418,328, filed Jan. 27, 2017, now U.S. Pat. No. 10,080,507, granted Sep. 25, 2018, which further claims priority to U.S. Provisional Patent Application No. 62/287,598, filed on Jan. 27, 2016. Priority to U.S. Provisional Patent Application No. 62/287,598 is expressly claimed, and the disclosures of each of the foregoing related applications is hereby incorporated by reference, in their entireties, for all purposes.

TECHNICAL FIELD

This application relates generally to the technical field of monitoring systems, and more particularly, to a monitoring system that detects physical changes without physical contact.

BACKGROUND OF THE INVENTION

The performance of a variety of monitoring systems may be affected by where a sensor or its parts are placed relative to a target (e.g., a human such as an adult, teen, child, or baby) that is being monitored. For example, certain monitoring systems may require a sensor to be in physical contact with a target and may further require a part (e.g., a power or data cable) to be connected from a sensor to a monitoring device. There may be other circumstances in which the sensor might be used to detect changes in occupancy of a vehicle seat. In this case the sensor might also sense vital signs—e.g., pulse and/or respiration—of a seat occupant without direct physical contact.

Known monitoring systems require a sensor to be directly in contact with a target. For example, a traditional electrocardiogram (ECG) uses external electrodes to detect a patient's ECG signal. The external electrodes are located on the ends of cables and must be physically placed on a patient and near the patient's heart. This often necessitates the use of conductive materials that may be inconvenient to hook up and use, especially for long-term monitoring of a relatively active patient. These devices have significant limitations. For example, the patient must be physically connected to the device. If the patient wants to leave his or her bed, the device needs to be detached from, and then re-attached to the patient on his/her return, often by a highly trained staff member. The inconvenience and the delays associated with setting up such monitoring systems are also not well-suited for monitoring more active targets, for example, a baby in a crib or a person driving a vehicle. Although there are monitoring systems incorporated into devices such as wristbands and armbands they still typically need to be directly in contact with the target, and often provide inaccurate information and limited functionality.

Accordingly, there is a need for a monitoring system that does not require a sensor to be directly in contact with a target. There is also a need for a monitoring system that can assist in the management of a target's health, fitness, sleep and diet by monitoring physiological changes in a person's body. There is further a need for a monitoring system suitable for long-term use that can sense changes in a target and provide timely and appropriate diagnostic, prognostic and prescriptive information.

SUMMARY

This invention includes systems and methods that allow detection of physical changes within a body without physical contact with, or attachment to, the body. A body is a mass of matter distinct from other masses. Non-limiting examples of a body include, for example, a human's body, an animal's body, a container, a car, a house, etc. These changes might be physiological events such as cardiac function in an animal or changes in the properties of a bulk material such as grain in a silo. These changes could be dimensional changes such as those caused by the function of organs in an animal, or changes in the composition of the material such as water content in lumber.

A key feature of the measurement technique used in this instrument is that the measurement may be done over an extended volume such that the changes of multiple phenomena may be observed simultaneously. For example, sensing two separate but related physiological parameters (e.g., pulse and respiration) may be accomplished concurrently. The region sensed by this instrument may be changed by sensor element design within the instrument. A further extension of bulk sensing capability is the opportunity to use sophisticated computer signature recognition software, such as wavelet-based approaches, to separate individual features from the composite waveform.

This application relates to U.S. Pat. No. 9,549,682, filed on Oct. 30, 2014, which is explicitly incorporated by reference herein in its entirety. This application also relates to U.S. Pat. No. 9,035,778, filed on Mar. 15, 2013, which is explicitly incorporated by reference herein in its entirety.

Disclosed subject matter includes, in one aspect, a system for detecting and analyzing changes in a body. The system includes an electric field generator configured to produce an electric field. The system includes an external sensor device, coupled to the electric field generator, configured to detect physical changes in the electric field, where the physical changes affect amplitude and frequency of the electric field. The system includes a quadrature demodulator, coupled to the electric field generator, configured to detect changes of the frequency of the output of the electric field generator and produce a detected response that includes a low frequency component and a high frequency component. The system includes a low pass filter, coupled to the quadrature demodulator, configured to filter out the high frequency component of the detected response to generate a filtered response. The system includes an amplitude reference source configured to provide an amplitude reference. The system includes an amplitude comparison switch, coupled to the amplitude reference source and the electric field generator, configured to compare the amplitude reference and the amplitude of the electric field to generate an amplitude comparison. They system includes a signal processor, coupled to the low pass filter and the amplitude comparison switch, configured to analyze the filtered response and the amplitude comparison response.

Disclosed subject matter includes, in another aspect, a method for detecting and analyzing changes in a body. The method includes establishing an electric field around a desired area of detection with an electric field generator. The method includes monitoring frequency of the electrical field with a quadrature demodulator. The method includes detecting changes in the frequency of the electric field with the quadrature demodulator. The method includes monitoring amplitude of the electric field. The method includes detecting changes in the amplitude of the electric field with an amplitude reference source.

Disclosed subject matter includes, in yet another aspect, a non-transitory computer readable medium having executable instructions operable to cause an apparatus to establish an electric field around a desired area of detection with an electric field generator. The instructions are further operable to cause the apparatus to monitor frequency of the electrical field with a quadrature demodulator. The instructions are further operable to cause the apparatus to detect changes in the frequency of the electric field with the quadrature demodulator. The instructions are further operable to cause the apparatus to monitor amplitude of the electric field. The instructions are further operable to cause the apparatus to detect changes in the amplitude of the electric field with an amplitude reference source.

Before explaining example embodiments consistent with the present disclosure in detail, it is to be understood that the disclosure is not limited in its application to the details of constructions and to the arrangements set forth in the following description or illustrated in the drawings. The disclosure is capable of embodiments in addition to those described and is capable of being practiced and carried out in various ways. Also, it is to be understood that the phraseology and terminology employed herein, as well as in the abstract, are for the purpose of description and should not be regarded as limiting.

These and other capabilities of embodiments of the disclosed subject matter will be more fully understood after a review of the following figures, detailed description, and claims.

It is to be understood that both the foregoing general description and the following detailed description are explanatory only and are not restrictive of the claimed subject matter.

BRIEF DESCRIPTION OF THE DRAWINGS

Various objects, features, and advantages of the disclosed subject matter can be more fully appreciated with reference to the following detailed description of the disclosed subject matter when considered in connection with the following drawings, in which like reference numerals identify like elements.

DETAILED DESCRIPTION

The manner in which materials behave in an alternating current ("AC") circuit usually is described in terms of the amount of energy stored in the material and the amount of energy dissipated in the material on a per cycle basis. Energy storage occurs in both electric and magnetic fields created by the current. Dissipation occurs in transformation, in the material, of electrical energy into thermal energy, i.e., heat. These properties can vary over a wide range depending on the material. In many materials the properties are predominantly one type.

Dissipation in some materials may be attributed to the magnetic field properties of a material and in other cases to the electric field properties. In more general cases, both of these mechanisms are present. Because of this, there is a convention in which the magnetic field storage properties and any related dissipation are combined in a vector sum and called permeability. Similarly, the vector sum of the electric field storage properties and associated dissipation is called permittivity. These vector sums are expressed as complex values in which the dissipation is the real component and field storage properties are the imaginary component. In the present disclosure, the aggregated change in properties of a body are detected and quantified by measuring changes in the body's electromagnetic properties.

Although the approach described here works by sensing changes in the electromagnetic properties, i.e. changes in both electric and magnetic properties, in some applications the significant changes occur in only one set of properties. For purposes of further discussion, the instrument in this invention detects changes in permittivity. Detection of any other suitable property or combination of properties that are appreciated by a person skilled in the art is also within the spirit and limit of the disclosed subject matter. The dissipative component of permittivity often is expressed as the loss tangent of the material, while the storage term is called capacitance. Measuring these properties is accomplished by sensing the change of phase and amplitude of an electric field generated by the instrument and caused by the aggregated properties of a body within the field.

Figure 1:
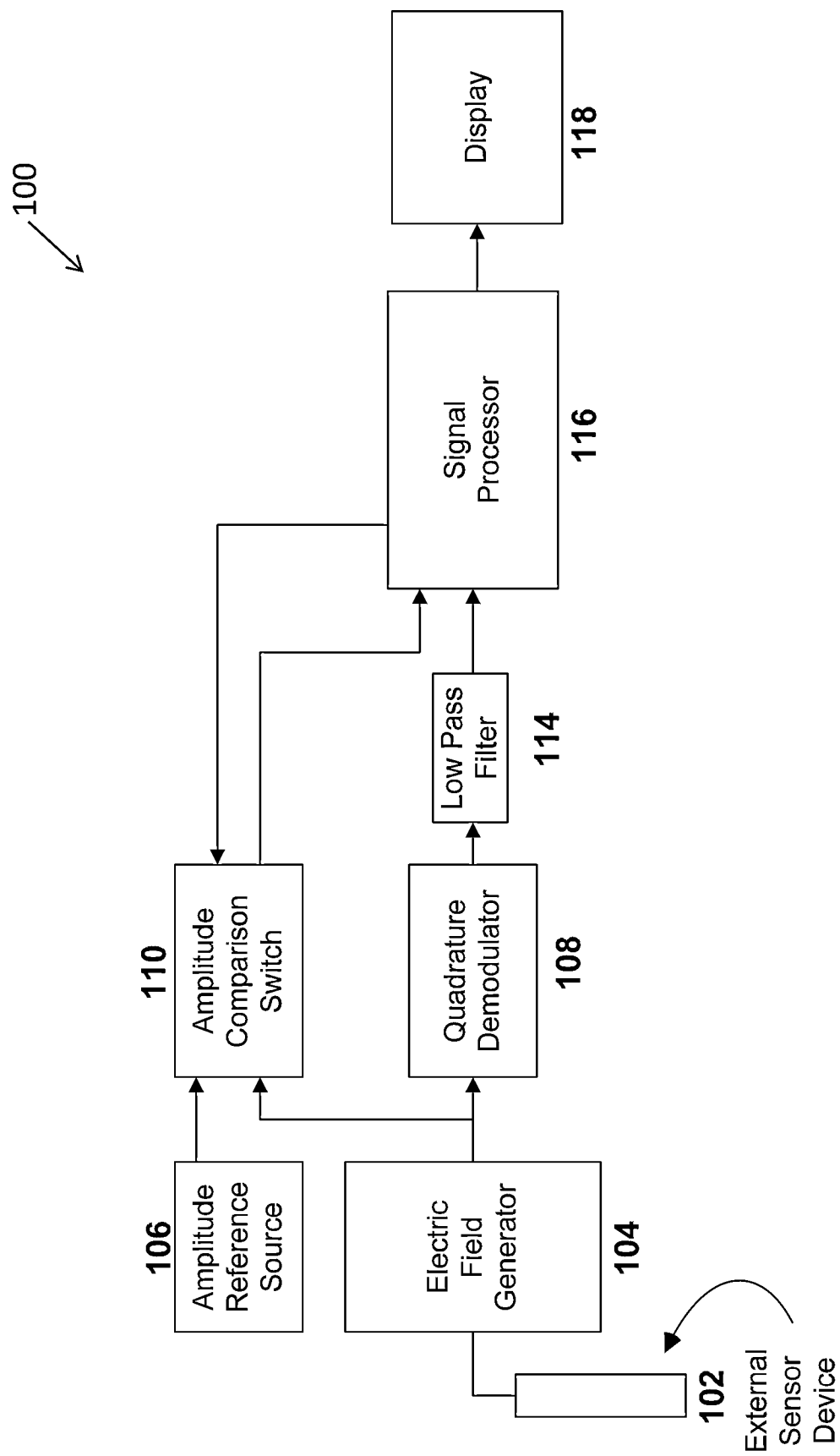
FIG. 1 illustrates a system for detecting and analyzing changes in a body according to certain embodiments of the present disclosure.

FIG. 1 illustrates a system 100 for detecting and analyzing changes in a body according to certain embodiments of the present disclosure. The system 100 includes an external sensor device 102, an electric field generator 104, an amplitude reference source 106, a quadrature modulator 108, an amplitude comparison switch 110, a low pass filter 114, a signal processor 116, and a display 118. The components included in the system 100 can be further broken down into more than one component and/or combined together in any suitable arrangement. Further, one or more components can be rearranged, changed, added, and/or removed. In some embodiments, one or more components of the system 100 can be made by an application specific integrated circuit (ASIC).

The electric field generator 104 creates an electric field that illuminates the desired area of detection. The frequency and amplitude of this electric field is determined by the characteristics of the body being observed. In some embodiments, a frequency-determining component of the electric field generator 104—a resonant circuit than can comprised of a combination of inductive, capacitive, and resistive elements—is connected to an external device that creates the electric field providing the desired coverage of the body of material being studied. In some embodiments, the electric field generator 104 can be an oscillator, such as an inductor-capacitor (LC) tank oscillator.

The external sensor device 102 may be made from a wide variety of materials; the only requirement of these materials is that they are electrical conductors. The external sensor device 102 can be constructed in many different mechanical configurations to provide appropriate coverage of the desired region. For example, in some embodiments, the external sensor device 102 can be a plurality of metallic plates. In some embodiments, the shape and/or the orientation of the external sensor device 102 can be changed as needed.

In some embodiments, the external sensor device 102 is not required to physically contact the body being studied. For example, the external sensor device 102 and the supporting electronics could be installed in the driver's seat of an over-the-highway truck to detect changes in physiological indicators of driver drowsiness and thus take actions to prevent an accident. In some embodiments, the sensing process usually is done separately in two paths: (1) in a first path the changes in the real component of the vector sum, e.g., energy dissipation, are detected; (2) in a second path the changes related to the imaginary component—a component such as a capacitance or inductance in which the phase of the current flowing in them is orthogonal to the current in the real component—are separately processed. In some embodiments, the changes in amplitude of the electric field are detected in the first path, and the changes in frequency of the electric field are detected in the second path. Generally, as known by a person skilled in the art, the changes in phase of the electric field can be obtained by analyzing the changes in frequency of the electric field. These two signals can be combined in later signal processing to re-create the changes in the complex permittivity or kept as individual signals for separate analysis. These two paths are discussed separately below.

Figure 6:
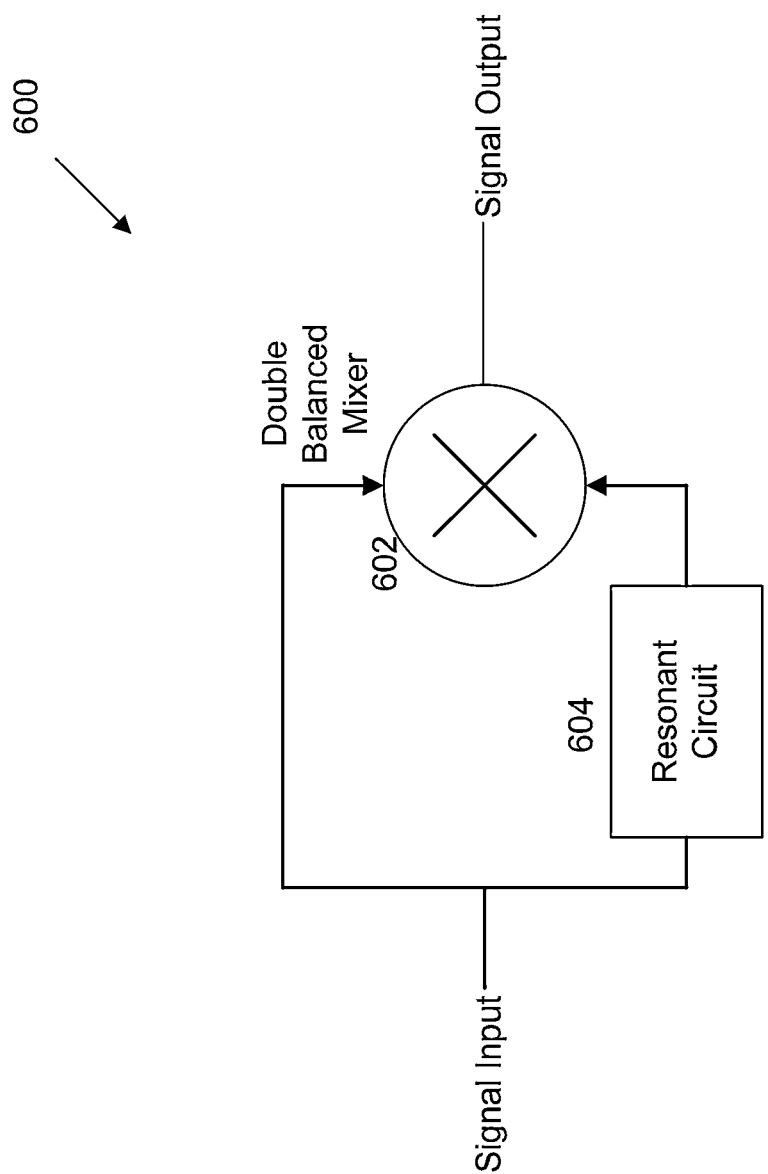
FIG. 6 illustrates a quadrature demodulator according to certain embodiments of the present disclosure.

To detect changes in the imaginary component of the complex permittivity, the output of the electric field generator 104 is connected to the quadrature demodulator 108. The quadrature demodulator 108 detects the changes of the frequency of the output of the electric field generator 104 and produce a detected response that includes a low frequency component and a high frequency component. FIG. 6 illustrates a quadrature demodulator 108 according to certain embodiments of the present disclosure. The quadrature demodulator 108 includes a mixer 602 and a resonant circuit 604. In the present disclosure, a double balanced mixer is described, but other suitable types of mixers can also be used. The components included in the quadrature demodulator 108 can be further broken down into more than one component and/or combined together in any suitable arrangement. Further, one or more components can be rearranged, changed, added, and/or removed.

An input signal to the quadrature demodulator 108 is split into two paths. One path is connected to one input port of the double balanced mixer 602, and the other path is connected to the resonant circuit 604. The output of the resonant circuit 604 is connected to the other input port of the double balanced mixer 602. In some embodiments, the resonant circuit 604 includes an inductor and a capacitor. In some embodiments, the resonant circuit 604 includes an inductor, a capacitor, and a resistor. The circuit components of the resonant circuit 604 can be connected in series, in parallel, or any other suitable configuration. The resonant circuit 604 can also be implemented by other circuit configurations that are appreciated by a person skilled in the art. In some embodiments, the resonant circuit 604 is tuned to the nominal center frequency of the electric field generator 104.

The double balanced mixer 602 multiplies the two signals together (one signal from the input and the other signal from the resonant circuit 604). The product of the two signals creates two components in the output: one proportional to the difference between the two input frequencies and another at the sum of the two input frequencies. When there is an exact 90-degree phase difference between the two signals, the demodulator output is zero. When the phase difference is less than about +/−90 degrees there will be a DC component in the output of the double balanced mixer 602.

The output signal from the quadrature demodulator 108 is fed to a low pass filter 114. The low pass filter 114 is typically an analog circuit that includes resistive, inductive and/or capacitive elements that separates the low frequency component of the quadrature modulator 108 from the much higher frequency component generated by the quadrature modulator 108. The cutoff frequency of the low pass filter is selected to provide low attenuation of the desired signal components while sufficiently suppressing the high frequency terms. After filtering, the signal is connected to the signal processor unit 116 described below.

Detecting changes in electric field dissipation is processed somewhat different from detecting frequency changes in electric field. In FIGS. 1 and 6, the output of the electric field generator 104 is multiplied by a phase-shifted version of itself produced by the resonant circuit 604. Unlike phase/frequency change detection, amplitude variations must be compared with the electric field generator 104 output unchanged by the material being studied. Referring again to FIG. 1, an amplitude reference signal is created by measuring the output of the electric field generator 104 in the absence of any external influence and used to set the output level of the amplitude reference source 106.

The amplitude reference source 106 is typically a time and temperature stable voltage reference that can be provided by a semiconductor component such as a diode. The output of the amplitude reference source 106 is fed to one input of the amplitude comparison switch 110. The switch 110, controlled by the signal processor 116, alternately connects the amplitude reference source 106 and electric field generator output 104 to the signal processor 116. By measuring the difference between the reference signal 106 and the electric field generator 104 output—and with sufficient calibration information—the amount of power absorbed, e.g., dissipated, by the material under study may be computed.

The amplitude comparison switch 110 functions by sampling the output of the electric field generator 104 at a rate at least twice as fast as the most rapid variation of the amplitude of the electric field generator 104 and subtracting the value of the amplitude reference source 106. The output of the amplitude comparison switch 110 is thus equal to the difference between the amplitude of the electric field generator 104 and the amplitude of the amplitude reference source 106.

The signal processor 116 takes the output of the low pass filter 114 and extracts the desired components into desired formats for further use or processing. The signal processor 116 also takes the output of the amplitude comparison switch 110 to analyze the changes in amplitude of the electric field. The signal processor 116 can be implemented by use of either analog, digital, or combined circuits.

Figure 7:
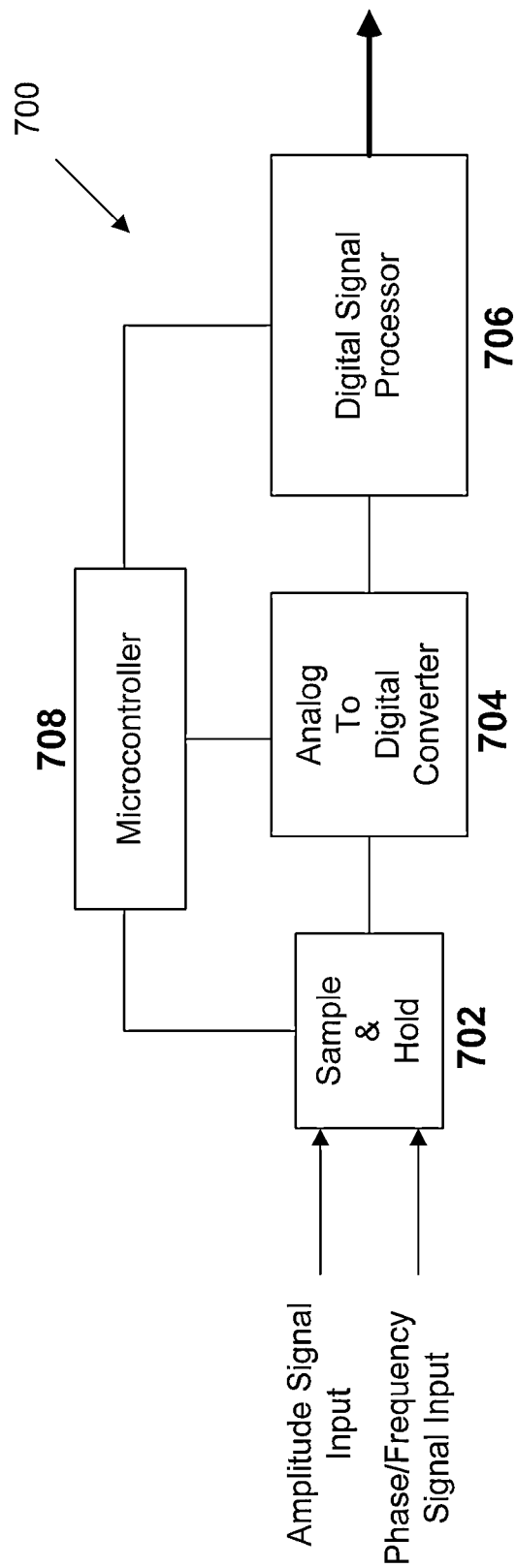
FIG. 7 illustrates a signal processor according to certain embodiments of the present disclosure.

FIG. 7 illustrates a signal processor 116 according to certain embodiments of the present disclosure. The signal processor 116 includes a sample-and-hold circuit 702, an analog-to-digital converter (ADC) 704, a digital signal processor 706, and a microcontroller 708. The components included in the signal processor 116 can be further broken down into more than one component and/or combined together in any suitable arrangement. Further, one or more components can be rearranged, changed, added, and/or removed.

The sample-and-hold circuit 702 is configured to sample a continuous-time continuous-value signal and hold the value for a specified period of time. A typical sample-and-hold circuit 702 includes a capacitor, one or more switches, and one or more operational amplifier. In some embodiments, other suitable circuit implementations can also be used.

The ADC 704 receives the output of the sample-and-hold circuit 702 and converts it into digital signals. In some embodiments, the ADC 410 can have a high resolution. Since the changes in bulk permittivity of the entire region within the electric field in many possible applications are expected to be relatively slow, e.g., less than a few hundred Hertz, in some embodiments it can be sufficient to undersample the output of the electric field generator 404 by using the sample-and-hold device 406 to make short samples that can be processed with the ADC 704 with a sample rate in the five thousand samples/sec range. An ADC with 24-bit resolution or 32-bit resolution are readily available. In some embodiments, the ADC 704 can have other suitable resolutions.

The digital signal processor 706 can be configured process the output of the ADC 704. In some embodiments, the digital signal processor 706 can be a microprocessor.

The microcontroller 708 can be coupled to one or more components of the signal processor 116. In some embodiments, the microcontroller 708 can control the sampling rate and/or clock rate of the one or more components of the signal processor 116. In some embodiments, the microcontroller 708 can issue command signals to the one or more components of the signal processor 116. In some embodiments, the microcontroller 708 can be a generic high performance low power system on chip (SOC) product. For example, the microcontroller 708 can be an ARM based processor, such as an ARM Cortex-M4 core processor or any other suitable models.

Referring to the display 118, the display 118 can be configured to display various results generated by the signal processor 116. The display 118 can be a touch screen, an LCD screen, and/or any other suitable display screen or combination of display screens. In some embodiments, the output of the signal processor 116 can also be fed to a data logger for signal storage and/or processing.

Figure 2:
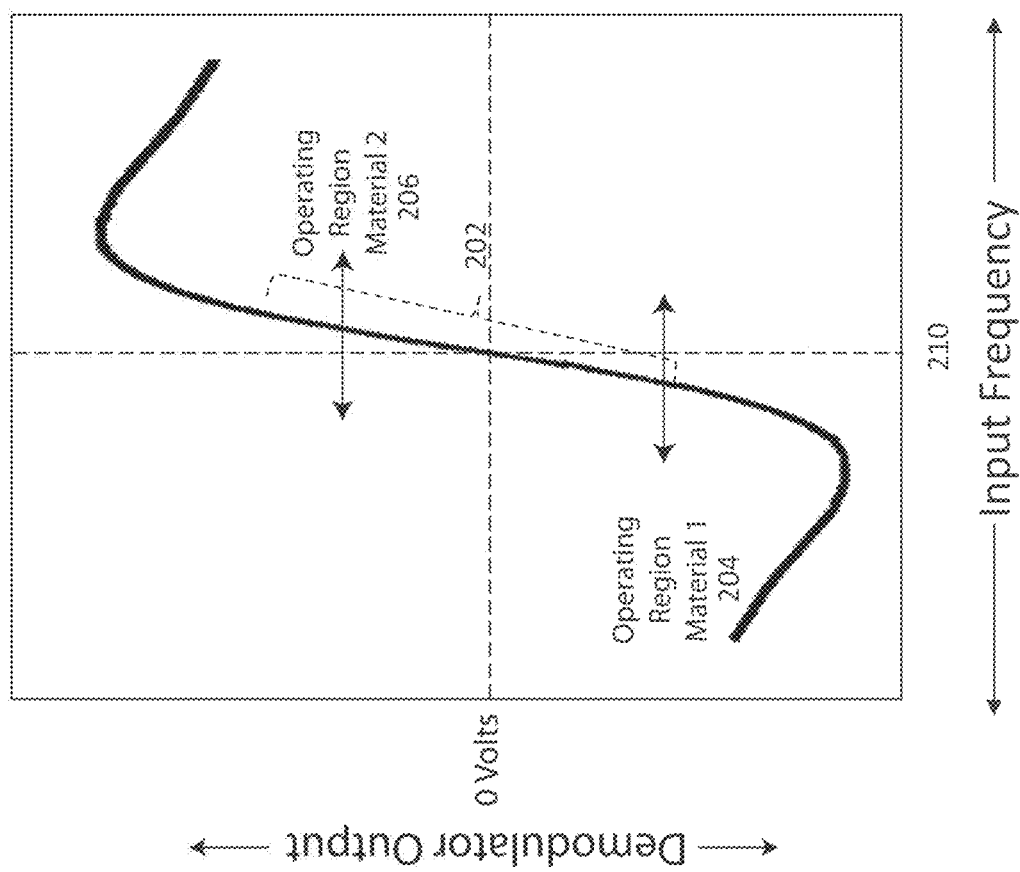
FIG. 2 illustrates a transfer function of a quadrature demodulator according to certain embodiments of the present disclosure.

FIG. 2 shows a generalized version of the transfer function of a quadrature demodulator 108 showing the typical relationship between the voltage output and frequency of the input signal from the electric field generator 104. The horizontal axis shows frequency of the input signal in Hertz (Hz), and the vertical axis shows demodulator output in Volts (V). The center of the horizontal axis 210 indicates the nominal resonant frequency of the resonant circuit 604. For example, if the nominal resonant frequency of the resonant circuit 604 is 80 MHz, then the center of the horizontal axis 210 is at 80 MHz. The slope of the central region 202 of the curve can be made quite linear to allow operation over an extended frequency range while offering the same sensitivity in terms of output voltage as function of phase/frequency change. The transfer function is mathematically dependent only on the frequency/phase relationship between the two inputs to the double-balanced mixer 108. This permits a wide and dynamic range in detection in the phase/frequency changes induced by material properties separate from changes in amplitude due to dissipative properties.

FIG. 2 illustrates the sensor operating as it might be employed in two different applications while using the same electric field generator 104 and the quadrature demodulator 108. In Region 1 204, the DC component—dependent on the exact value of the frequency and slope of the transfer function—might be, for example, −1.5 volts. If there are small variations in the frequency of the electric field generator 104, there will also be small variations in the quadrature demodulator output voltage. For the example here the output variations will be centered about −1.5 volts. In Region 2 206, the DC term might be, for example, around +1.0 volts. However, since the slope of the transfer function is very close to being the same in both regions, the small variations will be centered around 0 volts.

Figure 3:
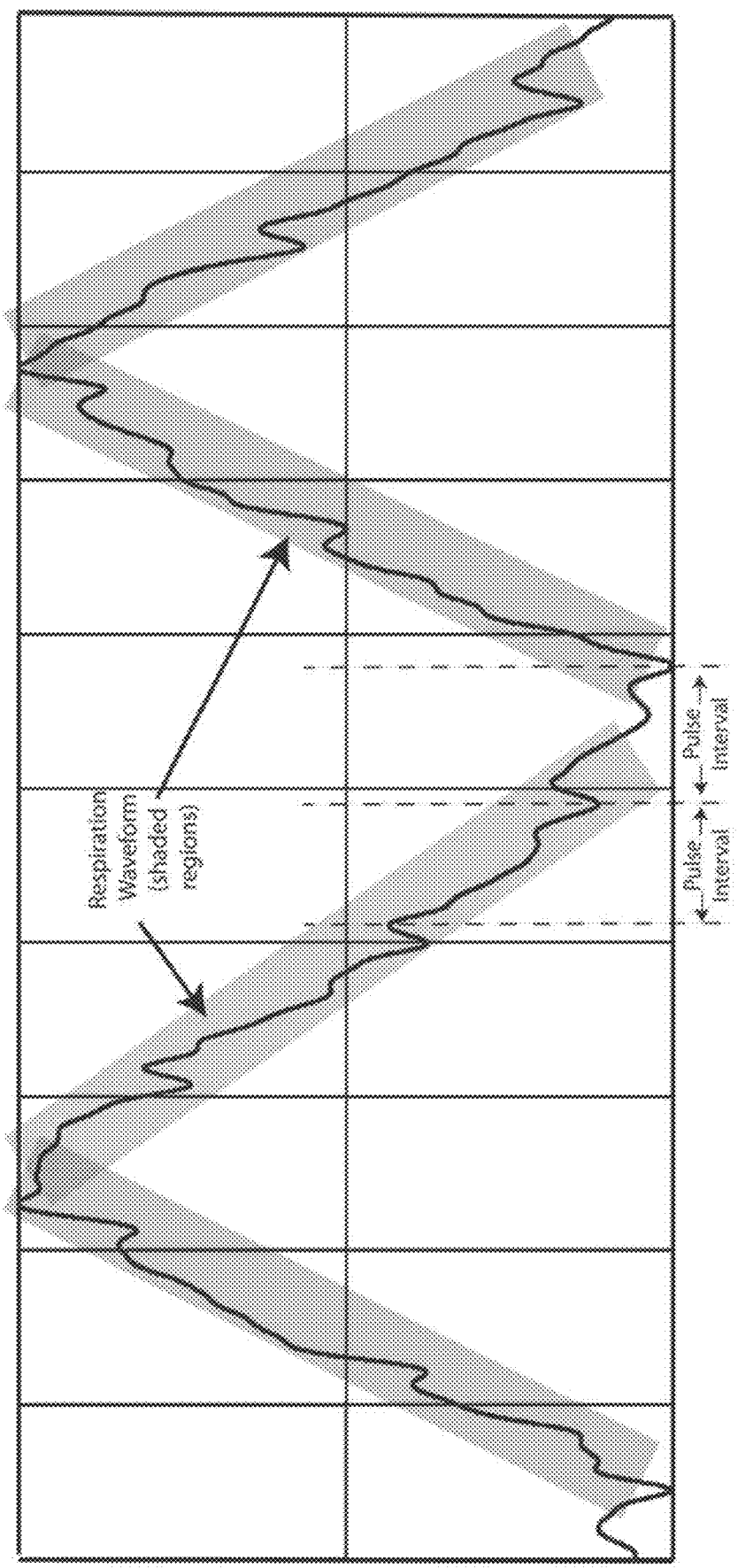
FIG. 3 illustrates a waveform combining both respiration and heart rate signals according to certain embodiments of the present disclosure.

This is an important benefit to the approach taken here. If there are a wide variety of materials, each with varying electromagnetic properties within the electric field, the aggregated output of the quadrature demodulator 108 can have a mean DC level determined by the contributions of all materials within the electric field region, while still maintaining an essentially constant transfer function for small changes in material properties. The small-signal linearity allows signal components from separate constituents of the material being studied to be linearly combined. Linear combination of the various contributions in the output waveform can be readily separated in later signal processing. An example of a combined waveform showing both respiration and heart rate (pulse) signals is shown in FIG. 3. The output signal from the quadrature demodulator-or other phase/frequency detector-is fed to a low pass filter 114. This low pass filter has two purposes: (1) it attenuates the high frequency spectral components arising from the multiplication of the two inputs to the double balanced mixer thus limiting any aliasing artifacts in subsequent digital signal processing; (2) it removes high frequency components close to the output of the phase/frequency detector preventing possible interference with other co-located apparatus. After filtering, the signal is connected to the signal processing unit 116 described below.

FIG. 3 shows a signal comprised of a large, low frequency, roughly triangular waveform that might be typical of respiration by a body and a signal often seen in a heart pulse of smaller amplitude, higher frequency, and more complex waveform. In FIG. 3 the linear addition of these two waveforms is shown as the smaller amplitude, higher frequency, more complex heart pulse "riding" on the larger, slower triangular respiration component.

Figure 4:
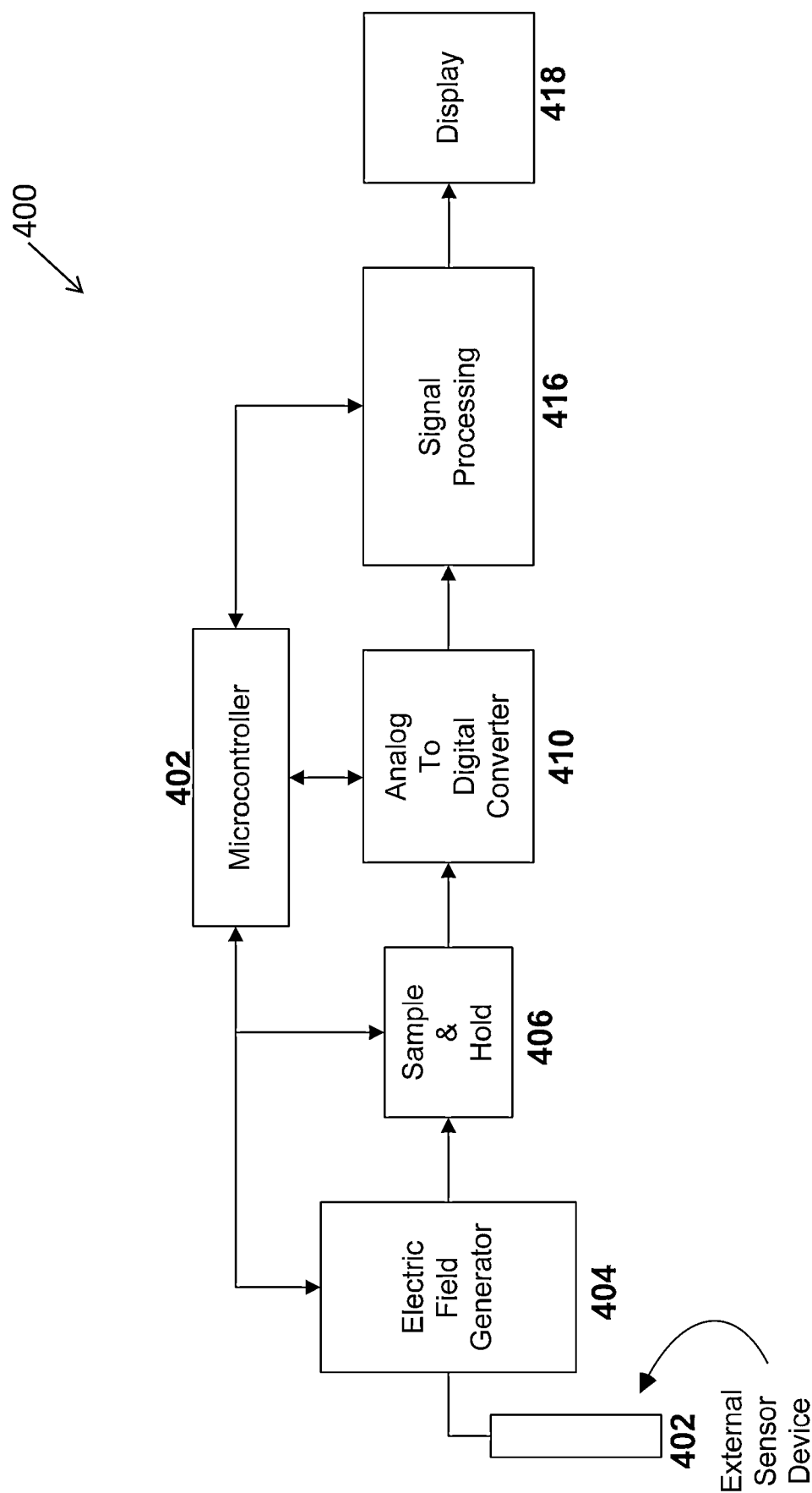
FIG. 4 illustrates a system for detecting and analyzing changes in a body according to certain embodiments of the present disclosure.

In addition to the largely analog design described above, a "direct-to-digital" approach is also possible. FIG. 4 illustrates a system 400 for detecting and analyzing changes in a body according to certain embodiments of the present disclosure. The system 400 includes an external sensor device 402, an electric field generator 404, a sample-and-hold device 406, a microcontroller 408, an ADC 410, a digital signal processor 416, and a display 418. The components included in the system 400 can be further broken down into more than one component and/or combined together in any suitable arrangement. Further, one or more components can be rearranged, changed, added, and/or removed. In some embodiments, the components included in FIG. 4 are similar to the corresponding components described in FIG. 1 and/or FIG. 7.

In some embodiments, the system 400 replaces most analog components described in FIG. 1 with digital or mixed-signal components. The "direct-to-digital" concept employs the ADC 410 driven by the sample-and-hold device 406. In some embodiments, the ADC 410 can have a high resolution. Since the changes in bulk permittivity of the entire region within the electric field in many possible applications are expected to be relatively slow, e.g., less than a few hundred Hertz, it can be sufficient to undersample the output of the electric field generator 404 by using the sample-and-hold device 406 to make short samples that can be processed with the ADC 410 with a sample rate in the five thousand samples/sec range. Such devices with 24-bit resolution are readily available, as are 32-bit versions at a significantly higher component price. In such a system, the signal processor 416 would take over the functions performed by the quadrature demodulator 108 described in FIG. 1. Since the features of the "direct-to-digital" instrument would be determined by the software in the signal processor 416, a single hardware set could be loaded with specialized software for different applications. The programmable characteristics of a "direct-to-digital" approach could enable economies of scale, driving down the unit cost and opening new market opportunities. In some embodiments, the ADC can be made by an application specific integrated circuit (ASIC).

Figure 5:
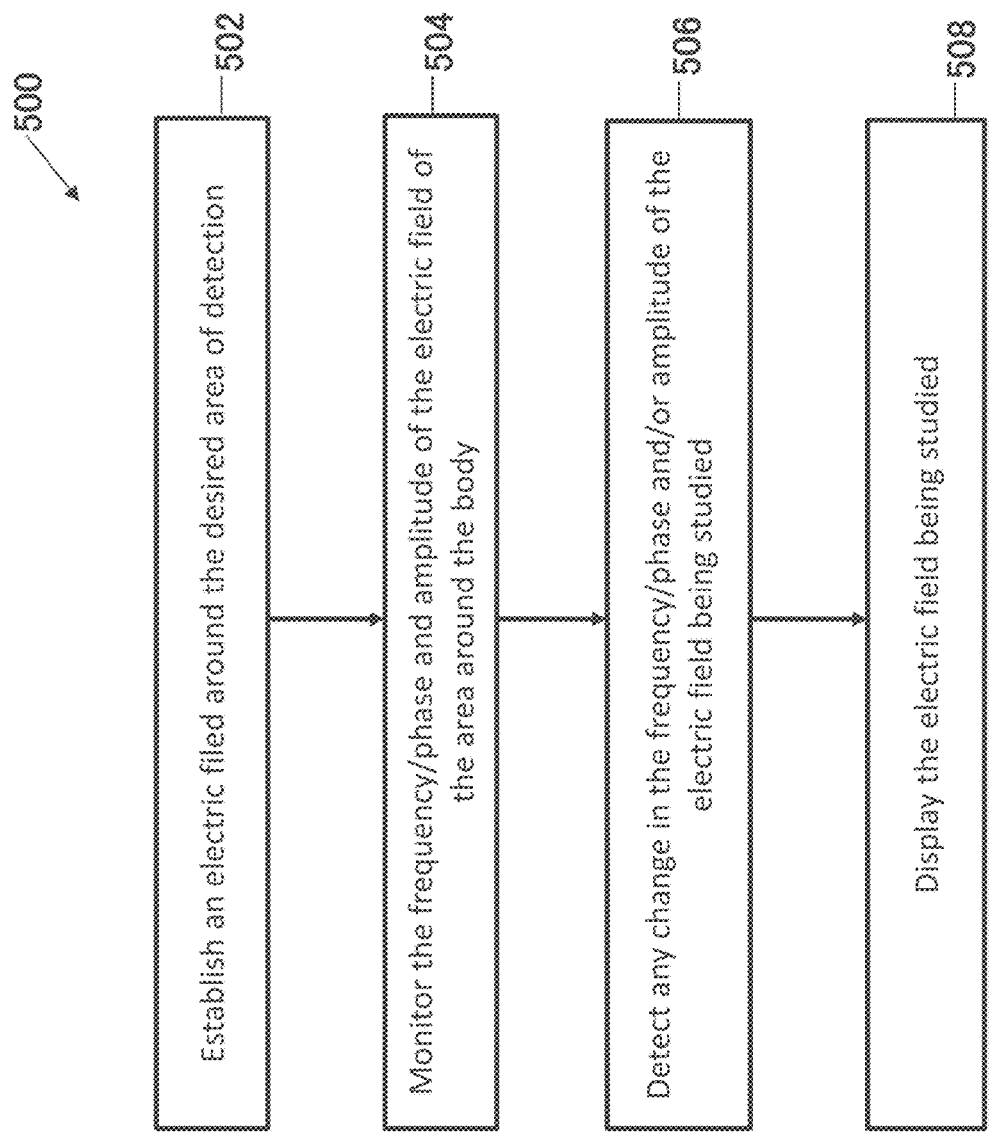
FIG. 5 illustrates a process of detecting and analyzing changes in a body according to certain embodiments of the present disclosure.

FIG. 5 is a flow chart illustrating a process 500 of detecting and analyzing changes in a body according to certain embodiments of the present disclosure. The process 500 is illustrated in connection with the system 100 shown in FIG. 1 and/or the system 400 shown in FIG. 4. In some embodiments, the process 500 can be modified by, for example, having steps rearranged, changed, added, and/or removed.

At step 502, an electric field is established around the desired area of detection. The desired area of detection is typically around a body that is going to be monitored. In some embodiments, the electrical field is established by using the electric field generator 104, which creates an electric field that illuminates the desired area of detection. The process 500 then proceeds to step 504.

At step 504, the frequency and amplitude of the electric field of the desired area of detection are monitored. In some embodiments, the external sensor device 102 is used to monitor the area around and within the body. The external sensor device 102 is not required to physically contact the body being studied. The process 500 then proceeds to step 506.

At step 506, the electric field of the desired area of detection is processed and analyzed to detect any change. The process 500 can detect the change of the electric field in both amplitude and frequency/phase. For example, amplitude variations of the electric field can be compared with the electric field generator 104 output unchanged by the material being studied. Referring again to FIG. 1, an amplitude reference signal is created by measuring the output of the electric field generator in the absence of any external influence and used to set the output level of the amplitude reference source 106. The output of the amplitude reference source 106 is fed to one input of the amplitude comparison switch 110. The switch 110, controlled by the signal processor 116, alternately connects the amplitude reference source 106 and electric field generator output 106 to the signal processor. By measuring the difference between the reference signal and the electric field generator 104 output—and with sufficient calibration information—the amplitude comparison response of the electric field can be determined.

The change of the electric field in frequency/phase can be detected and analyzed by the quadrature demodulator configuration discussed in connection with FIG. 1 and FIG. 6. For example, in some embodiments, the output of the electric field generator 104 is connected to the quadrature demodulator that is configured to detect the changes of the frequency of the output of the electric field generator 104 and produce a detected response that includes a low frequency component and a high frequency component. The detected response is then fed to a low pass filter 114 that is configured to filter out the high frequency component of the detected response to generate a filtered response. In some embodiments, once the changes in frequency is detected, the changes in phase can be readily derived by people skilled in the art.

The filtered response and the amplitude comparison response can then be supplied to a signal processor for further analysis.

In some embodiments, the change of the electric field can be analyzed under the "direct-to-digital" approach described in the system 400 in connection with FIG. 4. The output of the electric field generator 404 can be sampled and held by the sample-and-hold device 406 and digitized by the ADC 410. The digitized output of the ADC 410 can then be analyzed by the digital signal processor 416. The process 500 then proceeds to step 508.

At step 508, the electric field can be displayed for visual inspection. In some embodiments, the changes of the electric field can also be displayed and recorded. In some embodiments, the changes of the electric field can be extracted to provide specific bodily function features such as vascular processes and conditions, respiration processes and conditions, and other body material characteristics that vary with permittivity.

In some embodiments, the system 100 or the system 400 can include a processor, which can include one or more cores and can accommodate one or more threads to run various applications and modules. The software can run on the processor capable of executing computer instructions or computer code. The processor may also be implemented in hardware using an application specific integrated circuit (ASIC), programmable logic array (PLA), field programmable gate array (FPGA), or any other integrated circuit.

The processor can be couple with a memory device, which can be a non-transitory computer readable medium, flash memory, a magnetic disk drive, an optical drive, a PROM, a ROM, or any other memory or combination of memories.

The processor can be configured to run a module stored in the memory that is configured to cause the processor to perform various steps that are discussed in the disclosed subject matter.

The following applications and/or methods are non-limiting examples of applying the disclosed subject matter.

In some embodiments, changes in capacitor excitation frequency can be remotely sensed to alleviate the need for analog data reduction at the sensor.

In some embodiments, blood pressure can be measured by isolating a body region using a pressure "doughnut" and then releasing pressure and monitoring the return of blood flow as a result. Traditional means enclosing a limb to close an artery and monitor the pressure at which the artery opens up as the pressure is released. With the disclosed invention, a body region can be determined that excludes blood by closing capillaries (within the 'doughnut' pressure region) and monitoring the pressure at which they then open again. This simplification of application could then be applied to in-seat circumstances in hospital/clinic waiting rooms and the like.

In some embodiments, first derivatives can be used to find a recurring pattern in a combined time series signal of heartbeat and respiration such that the respiration signal can be subtracted from the combined signal to leave the heartbeat signal.

In some embodiments, the mathematical notion of Entropy (H) can be used to analyze a heartbeat signal and extract event timing information with respect to characterizing heart processes.

In some embodiments, wavelet analysis can be used to disambiguate complex time series data with highly variable frequency compositions. Signals that vary their frequency in time are resistant to effective analysis using traditional digital techniques such as fast Fourier transform (FFT). Wavelets provide the notion of short pattern correlation that can be applied to a sliding window of time series data in order to provide a second correlation time series that indicates the time at which a test pattern or "wavelet" is found within the first time series.

In some embodiments, a low resolution FFT can be used to peak search for power levels in a correlation function. This FFT power analysis is then used to set the correlation cutoff level and thus determine higher resolution correlated frequencies based on the power levels provides by the FFT. The FFT essentially filters out correlations below a particular power level so that more strongly correlated signals can remain. This provides a way of efficiently 'normalizing' the power levels relative to one another in trying to separate low frequency signals that are relatively close in frequency but widely separated in power without having to increase the resolution of the FFT with attendant significantly increased FFT window acquisition time.

In some embodiments, Kalman filters can be used to process the effect of changes in permittivity as indicated by a time series data such that the filter relates the predicted next value in a time series in maintaining a useable moving average for the purposes of normalizing a highly variable signal from a sensor with high dynamic range.

In some embodiments, measurement of the temperature of a body or substance can be obtained by measuring the permittivity of said body or substance where such permittivity may be correlated to temperature.

In some embodiments, measurement of the pressure within a body, substance, and/or liquid can be obtained by measuring the permittivity of said body, substance, and/or liquid where such permittivity may be correlated to pressure.

In some embodiments, stress levels in an individual can be determined by analyzing his or her motion, heartbeat characteristics and respiration using a remote, non-contact, biometric sensor.

In some embodiments, the quality of food in food processing and handling operations can be monitored by correlating the qualities of the food to the measured permittivity of the food item.

In some embodiments, the characteristics (e.g., turbulence, flow, density, temperature) of a fluid (e.g., paint, blood, reagents, petroleum products) can be monitored by correlating the characteristics of the fluid to the objective characteristics of the fluid.

In some embodiments, cavities and/or impurities in solid materials can be found. Such application can be used in areas such as the detection of delamination in composite materials, voids in construction materials, entrained contaminants, and/or the quality of fluid mixing.

In some embodiments, contraband enclosed within solid objects can be found.

In some embodiments, the life signs of infants in cribs, pushchairs and/or car seats can be monitored.

In some embodiments, the presence and life signs located in automobiles can be detected for the purposes of providing increased passenger safety, deploying airbags, and/or prevent baby from being left behind.

In some embodiments, the sentience of a driver can be detected by using heartbeat variability. In some embodiments, gestures such as the head-nod signature motion.

In some embodiments, the life signs in unauthorized locations (e.g., smuggling and/or trafficking) can be discovered.

In some embodiments, the quality of glass manufacture can be assessed by detecting variations in thickness, poor mixing, and/or the entrainment of impurities and/or.

In some embodiments, the nature of underground/subsurface texture and infrastructure (pipes and similar) can be assessed.

In some embodiments, the external sensor device disclosed herein can be combined with other sensors (e.g., camera, echolocation, pressure/weight/accelerometers) to provide enhanced sensor application using sensor "fusion."

In some embodiments, certain body conditions can be detected. The body conditions include conditions of the body relating to heart-lung functions, pulmonary fluid levels, blood flow and function, large and small intestine condition and process, bladder condition (full/empty) and process (rate fill/empty), edema and related fluid conditions, bone density measurement, and any other suitable condition or combination of conditions.

It is to be understood that the disclosed subject matter is not limited in its application to the details of construction and to the arrangements of the components set forth in the following description or illustrated in the drawings. The disclosed subject matter is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, systems, methods, and media for carrying out the several purposes of the disclosed subject matter.

Although the disclosed subject matter has been described and illustrated in the foregoing exemplary embodiments, it is understood that the present disclosure has been made only by way of example, and that numerous changes in the details of implementation of the disclosed subject matter may be made without departing from the spirit and scope of the disclosed subject matter.

What is claimed:

1. A system comprising:
   an electric field generator comprising an oscillator oscillating at a frequency, the electric field generator establishing an electric field around a desired area of detection that includes a body being monitored;
   a demodulator coupled to an output of the electric field generator and outputting a signal indicative of a change in a frequency of the generated electric field around the desired area of detection, wherein the demodulator multiplies the output of the electric field generator by a phase-shifted version of the output of the electric field generator, the phase-shifted version of the output of the electric field generator being generated by a resonant circuit; and wherein characteristics of the body being monitored cause the change in the frequency of the generated electric field around the desired area of detection.

2. The system of claim 1, further comprising:
an external sensor coupled to the electric field generator, the external sensor monitoring the frequency of the generated electric field around the desired area of detection.

3. The system of claim 1, further comprising a signal processor configured to analyze the change in the frequency of the generated electric field.

4. The system of claim 3, further comprising a low pass filter coupled between the demodulator and the signal processor.

5. The system of claim 3, wherein the signal processor is configured to separate a plurality of signal components in the output of the demodulator, each signal component associated with a separate constituent of the body.

6. The system of claim 5, wherein the plurality of signal components includes a heart rate signal and a respiration rate signal.

7. The system of claim 1, further comprising a display configured to provide a plurality of bodily function features based on the change in the frequency of the generated electric field, the bodily function features including a vascular process and a respiration process.

8. The system of claim 3, further comprising a sample-and-hold device coupled between the electric field generator and the signal processor.

9. The system of claim 3, wherein the signal processor comprises the demodulator.

10. A method comprising:
establishing, by an electric field generator, an electric field around a desired area of detection that includes a body being monitored, the electric field generator comprising an oscillator oscillating at a frequency; and
detecting, by a demodulator coupled to an output of the electric field generator, a change in a frequency of the generated electric field around the desired area of detection, wherein the detecting comprises multiplying the output of the electric field generator by a phase-shifted version of the output of the electric field generator, the phase-shifted version of the output of the electric field generator being generated by a resonant circuit;
wherein characteristics of the body being monitored cause the change in the frequency of the generated electric field around the desired area of detection.

11. The method of claim 10, further comprising:
monitoring, by an external sensor, the frequency of the generated electric field around the desired area of detection.

12. The method of claim 10, further comprising:
analyzing, by a signal processor, the change in the frequency of the generated electric field.

13. The method of claim 12, further comprising:
filtering an output of the demodulator using a low pass filter to generate a filtered response, and
providing the filtered response to the signal processor.

14. The method of claim 12, further comprising:
separating a plurality of signal components in an output of the demodulator, each signal component associated with a separate constituent of the body.

15. The method of claim 14, wherein the plurality of signal components includes a heart rate signal and a respiration rate signal.

16. The method of claim 10, further comprising:
providing a plurality of bodily function features based on the change in the frequency of the generated electric field, the bodily function features including a vascular process and a respiration process.

17. The method of claim 12, further comprising:
providing, to the signal processor, a signal based on a sampled response of the output of the electric field generator.

18. The method of claim 12, wherein the detecting is performed by the signal processor.

19. A non-transitory computer-readable medium containing instructions which when executed by a processor perform steps of:
generating, by an electric field generator, an electric field around a desired area of detection that includes a body being monitored, the electric field generator comprising an oscillator oscillating at a frequency; and
detecting, by a demodulator, a change in a frequency of the generated electric field, and wherein the detecting comprises analyzing an output of an analog-to-digital converter (ADC) coupled to a sample-and-hold circuit configured to sample an output of the electric field generator;
wherein characteristics of the body being monitored cause the change in the frequency of the generated electric field around the desired area of detection.

20. The non-transitory computer-readable medium of claim 19, wherein the steps further comprise:
separating a plurality of signal components in an output of the demodulator each signal component associated with a separate constituent of the body.

* * * * *

UNITED STATES PATENT AND TRADEMARK OFFICE
CERTIFICATE OF CORRECTION

| | |
|---|---|
| PATENT NO. | : 11,896,357 B2 |
| APPLICATION NO. | : 18/052655 |
| DATED | : February 13, 2024 |
| INVENTOR(S) | : John B. Langley, II et al. |

It is certified that error appears in the above-identified patent and that said Letters Patent is hereby corrected as shown below:

In the Claims

In Column 14, Line 47, in Claim 20, delete "demodulator" and insert -- demodulator, --.

Signed and Sealed this
Second Day of April, 2024

Katherine Kelly Vidal
Director of the United States Patent and Trademark Office